(12) United States Patent
Kozikowski et al.

(10) Patent No.: US 6,667,340 B1
(45) Date of Patent: Dec. 23, 2003

(54) INHIBITORS OF PHOSPHATIDYL MYO-INOSITOL CYCLE

(75) Inventors: Alan P. Kozikowski, Princeton, NJ (US); Lixin Qiao, Arlington, VA (US); Garth Powis, Tucson, AZ (US)

(73) Assignees: Arizona Board of Regents on behalf of the University of Arizona, Tucson, AZ (US); Georgetown University School of Medicine, Washington, DC (US)

( * ) Notice: Subject to any disclaimer, the term of this patent is extended or adjusted under 35 U.S.C. 154(b) by 0 days.

(21) Appl. No.: 09/879,765

(22) Filed: Jun. 12, 2001

Related U.S. Application Data

(63) Continuation-in-part of application No. 09/339,948, filed on Jun. 25, 1999, now Pat. No. 6,245,754.
(60) Provisional application No. 60/090,877, filed on Jun. 26, 1998, provisional application No. 60/223,421, filed on Aug. 7, 2000, provisional application No. 60/223,724, filed on Aug. 8, 2000, provisional application No. 60/235,269, filed on Sep. 26, 2000, and provisional application No. 60/235,270, filed on Sep. 26, 2000.

(51) Int. Cl.$^7$ ............................................. A61K 31/215
(52) U.S. Cl. ........................ 514/512; 514/546; 558/260; 560/129; 560/179; 560/186
(58) Field of Search ................................. 514/506, 529, 514/546, 512; 560/129, 179, 186; 558/260

(56) References Cited

PUBLICATIONS

J Med Chem 43, pp 3045–3051 by Hu et al Jul. 2000.*

\* cited by examiner

*Primary Examiner*—Jean F. Vollano
(74) *Attorney, Agent, or Firm*—Raymond A. Miller; Pepper Hamilton LLP

(57) ABSTRACT

The present invention relates to the preparation and biological activity of 3-deoxy-Dmyo-inositol ether lipid analogs as inhibitors of phosphatidylinositol-3-kinase signaling and cancer cell growth. The compounds of the present invention are useful as anti-tumor 5 agents which effectively inhibit the growth of mammalian cells.

9 Claims, 12 Drawing Sheets

30

INHIBITORS OF PHOSPHATIDYL MYO-INOSITOL CYCLE

RELATED APPLICATIONS

This is a continuation-in-part of application U.S. Ser. No. 09/339,948, filed on Jun. 25, 1999, now U.S. Pat No. 6,245,754, which claimed the benefit of priority from U.S. Provisional Patent Application Ser. No. 60/090,877, filed on Jun. 26, 1998; this application claims the benefit of U.S. Provisional Application Ser. No. 60/223,421, filed on Aug. 7, 2000, and U.S. Provisional Application Ser. No. 60/223,724, filed on Aug. 8, 2000, and U.S. Provisional Application Ser. No. 60/235,269, filed on Sep. 26, 2000, and U.S. Provisional Application Ser. No. 60/235,270, filed on Sep. 26, 2000.

BACKGROUND OF THE INVENTION

1. Field of the Invention

The present invention relates to specific compounds designed to inhibit cell growth signaling. In particular, PtdIns-3-kinase anti-metabolites are rationally designed to provide compounds that inhibit cell differentiation and/or cell proliferation, and/or which promote apoptosis by antagonizing myo-inositol cell growth signaling. The present invention also relates to therapeutic methods, e.g., treatment of cancer, including the administration of the compounds according to the invention.

2. Background of the Invention

For mammalian cells to survive, they must be able to respond rapidly to changes in their environment. Furthermore, for cells to reproduce and carry out other cooperative functions, they must be able to communicate efficiently with each other. Cells most frequently adapt to their environment and communicate with one another by means of chemical signals. An important feature of these signaling mechanisms is that in almost all cases a cell is able to detect a chemical signal without it being necessary for the chemical messenger itself to enter the cell. This permits the cell to maintain the homeostasis of its internal environment, thereby permitting the cell to respond to its external environment without being adversely affected by it.

These sensing functions are carried out by a variety of receptors, which are dispersed on the outer surface of the cell and function as "molecular antennae". These receptors detect an incoming messenger and activate a signal pathway that ultimately regulates a cellular process such as secretion, contraction, metabolism or growth. In the cell's cellular plasma membrane, transduction mechanisms translate external signals into internal signals, which are then carried throughout the interior of the cell by chemicals known as "second messengers."

In molecular terms, the process depends on a series of proteins within the cellular plasma membrane, each of which transmits information by inducing a conformational change in the protein next in line. At some point, the information is assigned to small molecules or even to ions within the cell's cytoplasm, which serve as the above-mentioned second messengers. The diffusion of the second messengers enables a signal to propagate rapidly throughout the cell.

Several major signal pathways are now known, but two seem to be of primary importance. One employs cyclic nucleotides as second messengers. These cyclic nucleotides activate a number of proteins inside the cell, which then cause a specific cellular response. The other major pathway employs a combination of second messengers that includes calcium ions as well as two substances whose origin is remarkable: myo-inositol-1,4,5-trisphosphate (IP3) and diacylglycerol (DAG). These compounds are cannibalized from the plasma membrane itself, by enzymes which are activated by specific cellular membrane receptors. However, this pathway requires that myo-inositol, in its non-phosphorylated form, be initially synthesized by the cell from glucose or obtained from the extracellular environment. Recently, another phosphatidylinositol signaling pathway has been identified and linked to the action of some growth factors and oncogenes. Phosphatidylinositol-3'-kinase (also designated type 1 phosphatidylinositol kinase) is found associated with a number of protein tyrosine kinases including the ligand-activated receptors for insulin, platelet derived growth factor (PDGF), epidermal growth factor (EGF), and colony-stimulating factor-1 (CSF-1) as well as proto-oncogene and oncogene tyrosine kinases (Y. Fukui et al., *Oncogene Res.*, 4, 283 (1989)). This enzyme phosphorylates the D-3 position of the myo-inositol ring of phosphatidylinositols to give a class of phosphafdylinositol-3'-phosphates that are not substrates for hydrolysis by phosphatidylinositol phospholipase C. Accordingly, these compounds apparently exert their signaling action independently of the inositol phosphate pathway.

Based on the potential effects thereof on cell proliferation, differentiation and apoptosis, it would be beneficial if compounds could be obtained which selectively block phosphatidylinositol signaling pathways. More specifically, it would be beneficial if compounds could be obtained which antagonize myo-inositol metabolites produced by PtdIns-3-Kinase. Such compounds have significant therapeutic potential, in particular for treatment of cancer and other conditions involving abnormal cell differentiation and proliferation. Compounds having improved selectivity, solubility and stability are particularly desirable.

SUMMARY AND OBJECTS OF THE INVENTION

It is an object of the invention to provide novel compounds which inhibit the phosphatidylinositol signaling pathway.

It is a more specific object of the invention to provide novel compounds which are antagonistic of myo-inositol metabolites provided by PtdIns-3-Kinase.

It is an even more specific object of the invention to provide novel analogs of 3-deoxy-D-myo-inositol which inhibit the phosphatidylinisitol signaling pathway.

It is still a more specific object of the invention to provide compounds having the formulae (I) and (II) set forth below:

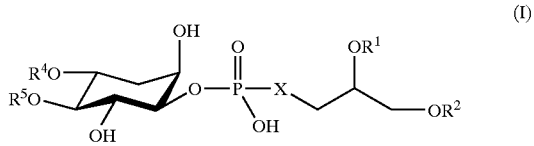

(I)

wherein X is O or $CH_2$; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl or $(C_9-C_{32})$ alkenylaryl, with the proviso that when X is O, $R^3$ is not $(C_{15})$ alkyl; $R^4$ and $R^5$ are individually hydrogen or a phosphate group; or when $R^4$ or $R^5$ is not hydrogen, a pharmaceutically acceptable salt thereof; and

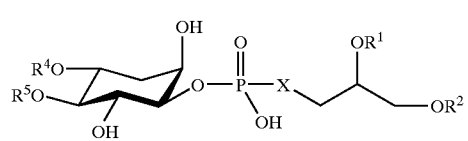
(II)

wherein X is O or $CH_2$,; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary aralkenyl or $(C_9-C_{32})$ alkenylaryl; $R^4$ and $R^5$ are individually hydrogen or a phosphate group; or when $R^4$ or $R^5$ is not hydrogen, a pharmaceutically acceptable salt thereof.

It is a more specific object of the invention to treat cancer by the administration of at least one compound of the formulae (I) or (II):

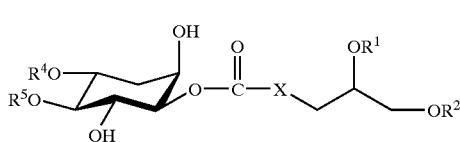
(I)

wherein X is O or $CH_2$; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl or $(C_9-C_{32})$ alkenylaryl, with the proviso that when X is O, $R^3$ is not $(C_{15})$ alkyl; $R^4$ and $R^5$ are individually hydrogen or a phosphate group; or when $R^4$ or $R^5$ is not hydrogen, a pharmaceutically acceptable salt thereof; and

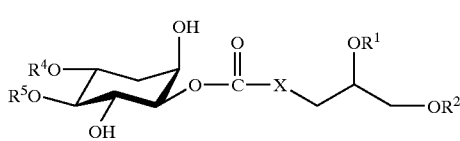
(II)

wherein X is O or $CH_2$; $R^1$ and R are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl, $(C_9-C_{32})$ alkenylaryl or $C(O)R^3$; and $R^3$ is $(C_1-C_{25})$ alkyl, $(C_6-C_{10})$) aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl or $(C_9-C_{32})$ alkenylaryl; $R^4$ and $R^5$ are individually hydrogen or a phosphate group; or when $R^4$ or $R^5$ is not hydrogen, a pharmaceutically acceptable salt thereof.

It is another object of the invention to provide pharmaceutical compositions comprising at least one novel compound that inhibits the phosphatidylinositol signaling pathway, and more preferably a compound that antagonizes myo-inositol metabolites produced by PtdIns-3-Kinase.

It is a more specific object of the invention to provide pharmaceutical compositions that comprise at least one compound having the formulae (I) or (II):

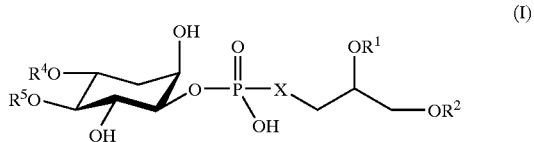
(I)

wherein X is O or $CH_2$; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary, $(C_9-C_{32})$ aralkenyl or $(C_9-C_{32})$ alkenylaryl, with the proviso that when X is O, $R^3$ is not $(C_{15})$ alkyl; $R^4$ and $R^5$ are individually hydrogen or a phosphate group; or when $R^4$ or $R^5$ is not hydrogen, a pharmaceutically acceptable salt thereof; or

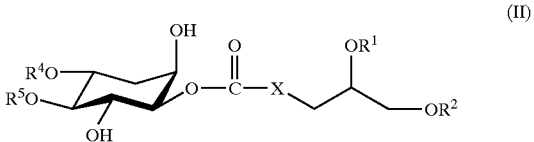
(II)

wherein X is O or $CH_2$; $R^1$ and $R^2$ are individually, $(C19-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary, $(C_9-C_{32})$ aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary, $(C_9-C_{32})$ aralkenyl or $(C_9-C_{32})$ alkenylaryl; $R^4$ and $R^5$ are individually hydrogen or a phosphate group; or when $R^4$ or $R^5$ is not hydrogen, a pharmaceutically acceptable salt thereof; which inhibit the phosphatidylinositol signaling pathway and thereby inhibit cell proliferation and/or differentiation and/or promote apoptosis.

It is another object of the invention to provide novel therapies based on inhibiting in vivo the phosphatidylinositol signaling pathway.

It is a more specific object of the invention to provide novel therapies that result in the inhibition of cell proliferation and/or differentiation and/or the promotion of cell apoptosis comprising the administration of a compound that antagonizes myo-inositol cell growth signaling.

It is an even more specific object of the invention to provide novel therapies that result in the inhibition of cell proliferation and/or differentiation and/or promotion of cell apoptosis by the administration of a compound having formulae (I) or (II):

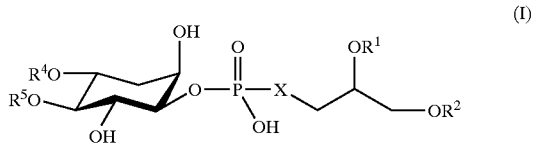
(I)

wherein X is O or $CH_2$; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylary, ($C_9$–$C_{32}$) aralkenyl, ($C_9$–$C_{32}$) alkenylaryl or C(O)$R^3$; and $R^3$ is ($C_1$–$C_{25}$) alkyl, ($C_6$–$C_{10}$) aryl, ($C_3$–$C_8$) cycloalkyl, ($C_2$–$C_{22}$) alkenyl, ($C_5$–$C_8$) cycloalkenyl, ($C_7$–$C_{32}$) aralkyl, ($C_7$–$C_{32}$) alkylaryl, ($C_9$–$C_{32}$) aralkenyl or ($C_9$–$C_{32}$) alkenylaryl, with the proviso that when X is O, $R^3$ is not ($C_{15}$) alkyl; $R^4$ and $R^5$ are individually hydrogen or a phosphate group; or when $R^4$ or R is not hydrogen, a pharmaceutically acceptable salt thereof; or

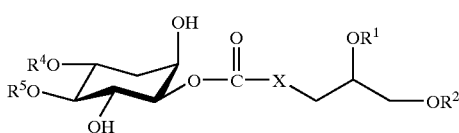

(II)

wherein X is O or $CH_2$; $R^1$ and $R^2$ are individually, ($C_1$–$C_{25}$) alkyl, ($C_6$–$C_{10}$) aryl, ($C_3$–$C_8$) cycloalkyl, ($C_2$–$C_{22}$) alkenyl, ($C_5$–$C_8$) cycloalkenyl, ($C_7$–$C_{32}$) aralkyl, ($C_7$–$C_{32}$) alkylaryl, ($C_9$–$C_{32}$) aralkenyl, ($C_9$–$C_{32}$) alkenylaryl or C(O)$R^3$; and $R^3$ is ($C_1$–$C_{25}$) alkyl, ($C_6$–$C_{10}$) aryl, ($C_3$–$C_8$) cycloalkyl, ($C_2$–$C_{22}$) alkenyl, ($C_5$–$C_8$) cycloalkenyl, ($C_7$–$C_{32}$) aralkyl, ($C_7$–$C_{32}$) alkylaryl, ($C_9$–$C_{32}$) aralkenyl or ($C_9$–$C_{32}$) alkenylaryl; $R^4$ and $R^5$ are individually hydrogen or a phosphate group; or when $R^4$ or $R^5$ is not hydrogen, a pharmaceutically acceptable salt thereof.

In a preferred embodiment, such therapies will comprise treatment of cancer and other neoplastic conditions and/or will comprise treatment of arthritis, inflamation or modulation of platelet aggregation.

DETAILED DESCRIPTION OF THE INVENTION

Figure 1:
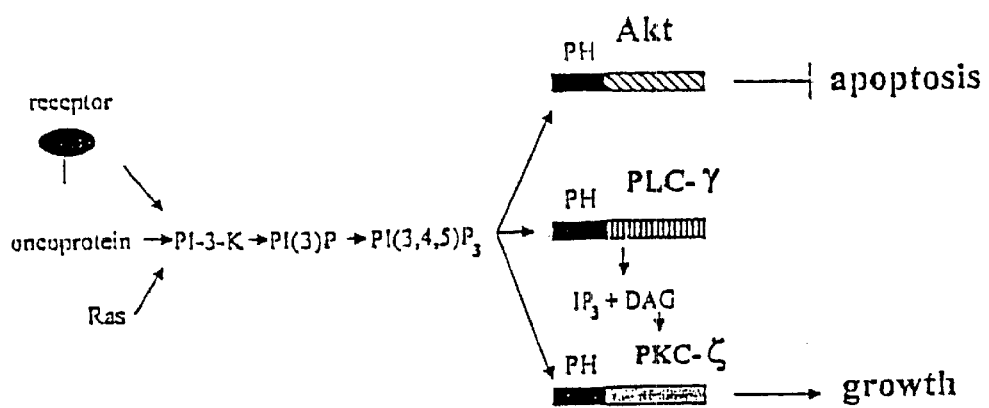
FIG. 1 is a schematic diagram of the signaling by PtdIns-3-kinase leading to cancer cell proliferation.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The present invention includes novel compounds which are rationally designed to inhibit cell growth. Rational design of the novel compounds of the present invention includes identifying a mechanism associated with cell growth. Information relating to the mechanism is then analyzed such that compound structures having possible activity in interfering with such mechanism are formulated. In particular, novel structures are synthesized based on "building blocks", wherein each building block. has a feature potentially capable of interfering with a particular mechanism associated with cell growth. Compounds having different building block combinations are then synthesized and their activity in relation to the identified mechanism tested. Such tests are conducted in vitro and/or in vivo. The information obtained through such tests is then incorporated in a new cycle of rational drug design. The design-synthesis-testing cycle is repeated until a lead compound having the desired properties is identified. The lead compound is then clinically tested.

Identification of a Mechanism Associated With Cell Growth

Growth factors and certain oncogenes activate a range of phospholipid-mediated signal transduction pathways associated with cell proliferation. Phosphatidyl myoinositol (PI) occupies a unique position in that it can undergo reversible phosphorylation at multiple sites to generate five different phosphoinositides. PI metabolites regulate two pathways important for cell proliferation, the inositol phosphate/diacylglycerol signaling pathway and the phosphate/diacylglycerol 3-phosphate (PI-3-kinase) pathway.

In the first pathway, PI specific phospholipase C (PI-PLC) hydrolyses a minor membrane phospholipid, PI(4,5)$P_2$ to give the water soluble Ins(1,4,5)$P_3$, and a lipophilic diacylglycerol (DAG). Ins(1,4,5)$P_3$ interacts specifically with membrane receptors to release $Ca^{2+}$, a key event in cellular signal transduction. DAG is an endogenous activator of protein kinase C (PKC). Ins(1,4,5)$P_3$ is metabolized either by hydrolysis of the phosphate at position 5, giving Ins(1,4)$P_2$ or phosphorylation at position 3 giving Ins(1,3,4,5)$P_4$. Ins(1,4)$P_2$ is not active as a $Ca^{2+}$ mobilizing agent and is subsequently degraded by other phosphatases. However, it has been suggested that Ins(1,3,4,5)$P_4$ may play a role in refilling the intracellular $Ca^{2+}$ stores with extracellular $Ca^{2+}$. Together, the increase in $Ca^{2+}$ concentration and the increased activity of PKC lead to a sequence of events that culminate in DNA synthesis and cell proliferation.

In the second pathway, PI-3-kinase has been found to be associated with almost every growth factor receptor or oncogene transformation. PI-3-kinase phosphorylates PI at position 3 of the myo-inositol ring to give a class of PIs that are poor substrates for hydrolyses by PI-PLC, e.g., PI(3,4)$P_2$ and PI (3,4,5)$P_3$.

PtdIns-3-kinases are a family of enzymes that phosphorylate the D-3-OH position of the myo-inositol ring of the minor cell membrane phospholipid phosphatidylinositol (PtdIns). The most studied member of the PtdIns-3-kinase family is a heterodimer consisting of an 85 kDa regulatory subunit (p85) and a 110 kDa catalytic subunit (p110). All of the known isoforms of p110 are capable of phosphorylating both PtdIns and PtdIns(4)P in vitro, however, PtdIns (4,5)$P_2$ is the preferred substrate in vivo. PtdIns-3-kinase is activated by a wide range of growth factor receptor and oncogene proteintyrosine kinases as well as by p21$^{Ras}$.

The exact mechanism by which 3-phosphorylated PIs modulate cell growth is not known but they appear to be important modulators of protein interaction and enzyme activity through binding to specific sites on proteins. For example, binding of PI(3,4)P$_2$ PI(4,5)P$_2$ or PI(3,4,5)P$_3$ to pleckstrin-homology (PH) domains on enzymes such as Akt (protein kinase B) leads to enzyme activation, whereas the Src-homology-2 (SH2) domain that mediates protein tyrosine phosphate binding binds specifically PI(3,4,5)P$_3$. PtdIns-3-kinase is activated by binding of the src-homology 2 (SH2) domain of the p85 regulatory subunit of PtdIns-3-kinase to phosphorylated tyrosine residues on activated growth factor receptors and oncogenic protein tyrosine kinases which cause a conformational change at the active site of the p110 catalytic subunit and brings PtdIns-3-kinase from the cytoplasm to the inner surface of the plasma membrane where PtdIns substrates are located. Also, PtdIns-3-kinase itself becomes tyrosine phosphorylated, however, this phosphorylation apparently does not result in any increased activity of the enzyme.

FIG. 1 depicts schematically the means by which PtdIns-3-kinase signaling is theorized to enhance cancer cell proliferation. Essentially, activation of PtdIns-3-kinase (PI-3-K) leads to the formation of PtdIns-3-phosphates which bind to the PH domains of enzymes such as Akt, PtdIns PLC-γ and activation of PKC-ζ.

Several lines of evidence suggest an essential role for PtdIns-3-kinase in the modulation of cancer cell growth and the cancer phenotype. For example, cells transfected with a mutant PDGF receptor that retains protein tyrosinekinase activity, but which do not associate with or activate Ptdfns-3-kinase, fail to show a mitogenic response to PDGF, unlike cells transfected with the wild-type PDGF receptor ("Role of phosphatidylinositol kinase in PDGF receptor signal transduction"; Coughlin et al.; *Science*, 243:1191–1194 (1989)). Also, it has been reported that a mutant CSF-1 receptor which contains a kinase-insert deletion results in significantly reduced association with PtdIns-3-kinase. Moreover, this mutant receptor is only capable of conferring CSF-1-dependent transformation to some cells and has lost the ability to transform other cells ("Phosphatidylinositol-3-kinase is necessary for 12-O-tetradecanoylphorbol-13-acetate-induced cell transformation and activated protein 1 activation"; Huang et al.; *J. Biol. Chem.*, 272:4187–4194 (1997)).

Further, it has been reported that active PtdIns-3-kinase is necessary for phorbol ester mediated transformation of cells. In particular, it has been reported that polyoma middle T mutants which associate with and activate pp60$^{c-src}$ tyrosine kinase, but which fail to activate PtdIns-3-kinase are non-transforming ("Common elements in growth factor stimulation and oncogenic transformation: 85 kd phosphoprotein and phosphatidylinositol kinase activity"; Kaplan et al.; *Cell*, 50:1021–1029 (1987)). It is further known that the levels of cellular PtdIns-3-phosphates are elevated in transforming mutants of middle T but not by transformation of defective mutants, suggesting that these compounds play a significant role in transformation.

It is also known that PtdIns-3-kinase prevents apoptosis and is necessary for the inhibition of apoptosis caused by nerve growth factor in PC 12 phemochromocytoma cells ("Requirement for phosphatidylinositol-3-kinase in the prevention of apoptosis by nerve growth factor"; Yao et al.; *Science*, 267:2003–2006 (1995)) and by IL-3 and IL-4 in 5 hematopoietic cells ("Signaling through the lipid products of phosphoinositide-3-OH kinase"; Toker et al.; *Nature*, 387:673–676 (1997)).

Based on the foregoing, PtdIns-3-kinase has generated considerable interest as a target for the development of anticancer drugs to block the activity of increased growth factor signaling or oncogene expression. More particularly, based on what has been reported about this enzyme, disease conditions that potentially would be susceptible to growth inhibition by PtdIns-3-kinase inhibitors include cancers that over-express PDGF receptors such as colon, pancreatic, prostate and head and neck tumors, and tumors overexpressing EGF receptor such as breast, gastric and prostate tumors. Also, tumors expressing mutant ras such as colon and pancreatic cancer and CML which is characterized by a Bcr/Abl (Philadelphia chromosome) translocation (where Bcr/Abl has been shown to require PtdIns-3-kinase for its effects) may also be amenable to treatment by compounds that affect PtdIns-3-kinase activity.

Essentially, because of the important role PtdIns-3-kinase apparently plays in effecting cell growth, it provides an exciting avenue for designing therapeutic protocols based on controlling PtdIns-3-kinase activity. More specifically, compounds which mediate PtdIns-3-kinase activity potentially may be used to control (inhibit) tumor cell growth.

A direct approach for modulating PtdIns-3-kinase and the biological pathways it affects is to design therapeutic protocols based on compounds having PtdIns-3-kinase inhibitory activity. Supplying such compounds to target cells potentially should reduce or block cell proliferation attributable to the inhibition of PtdIns-3-kinase.

An example thereof is the fungal metabolite wortmannin, which is an irreversible 20 inhibitor of p110 PtdIns-3-kinase (having an IC$_{50}$ of 4 nM) ("Wortmannin inactivates phosphoinositide 3-kinase by covalent modification of Lys-802, a residue involved in the phosphate transfer reaction"; Wymann et al.; *Mol. Cell Biol*, 16:1722–1733 (1996)). Because of this activity, wortmannin has been used extensively as a pharmacological probe of the functions of PtdIns-3-kinase. Based on such inhibitory activity, it was initially hoped that wortmannin might be a useful anticancer drug against tumors with activated PtdIns-3-kinase signaling ("In vitro and in vivo activity of the phosphatidylinositol-3-kinase inhibitor, wortmannin"; Schultz et al.; *Anticancer Res.*, 15:1135–1140 (1995)).

Unfortunately, while although wortmannin has shown anti-tumor activity against a variety of tumors, it lacks target selectivity and is toxic to normal tissues, particularly the liver and hematopoietic system. This has precluded its further therapeutic development. Such lack of selectivity is apparently attributable to the fact that wortmannin inhibits other serine/threonine kinases of the PtdIns-3-kinase family, e.g., mTOR and DNA-dependent protein kinase, with IC$_{50}$s of 2 to 4 nM. The unrelated enzyme phospholipase A2 is also inhibited by wortmannin, with an IC$_{50}$ of 2 nM ("Wortmannin and its structural analogue demethoxyviridin inhibit stimulated phospholipase A$_2$ activity in Swiss 3T3 cells"; Cross et al.; *J. Biol. Chem.*, 270:25352–25355 (1995)).

The poor selectivity of PtdIns-3-kinase inhibition by wortmannin suggests that the binding site of PtdIns-3-kinase does not have unique structural features recognizable by this inhibitor. This, in turn suggests that designing PtdIns-3-kinase inhibitors having acceptable selectivity requires detailed structural analysis of the active sites of PtdIns-3kinase and related enzymes whose activity is indiscriminately inhibited by known inhibitors such as wortmannin.

Another potential approach for controlling PtdIns-3-kinase activity and thereby cell growth which is the focus of the present invention, is directed to PtdIns-3-kinase metabolites. More specifically, the subject approach is based on rationally designing compounds which are antagonists of myo-inositol second messengers produced by PtdIns-3-kinase which reduce or block cell growth by antagonizing myo-inositol cell growth signaling. Preferably, antagonists are designed which reduce or block cell proliferation while leaving other aspects of myo-inositol signaling unaffected. The designed antagonists should provide a novel basis for therapeutic protocols based on the selective control of cancer cell growth signaling which do not disrupt the function of normal cells.

Metabolic Products of Phosphatidylinositol-3-kinase

The products of PtdIns-3-kinase, i.e., PtdIns-3-phosphates, are responsible for the effects of PtdIns-3-kinase on tumor growth and apoptosis. Only recently has their mechanism of action begun to be understood. PtdIns-3-phosphates are found in the cell as small amounts of PtdIns-3-phosphate and larger amounts of $PtdIns(3,4)P_2$ and $PtdIns(3,4,5)P_3$ ("Phosphoinositide 3-kinase is activated by phosphopeptides that bind to the SH2 domains of 84-kDa subunit"; Carpenter et al.; *J. Biol. Chem.*, 268:9478–9483 (1993)). PtdIns-3-phosphates have the unique ability to bind to specific protein domains, a property not shared by non-3-phosphorylated PtdIns, resulting in the activation of key signaling proteins involved in cell growth and death. The pleckstrin homology (PH) domain is a protein module of approximately 120 amino acids found in a number of signaling proteins activated by PtdIns-3-phosphate binding. The PH domain of these proteins binds specifically to PtdIns-3-phosphates present in the inner plasma membrane resulting in. the translocation of the signaling proteins from the cytosol to the plasma membrane where their substrates are located. Binding of PtdIns-3-phosphates to PH domains may also result in a direct increase in the catalytic activity of the enzyme ("PH domains: diverse sequences with a common fold recruit signaling molecules to the cell surfaces"; Lemmon et al.; *Cell*, 85:621–624 (1996)).

The most extensively studied examples of PH domain-regulated signaling are the PH domain dependent activation by $PtdIns(3,4)P_2$ and $PtdIns(3,4,5)P_3$ of the serine/threonine kinase Akt (PKB/Rac) and of PtdIns-PLCγ. Binding of the PH domain to membrane PtdIns-3-phosphates causes the translocation of Akt to the plasma membrane bringing it into contact with membrane bound Akt kinase, which is itself activated by $PtdIns(3,4,5)P_3$, which then phosphorylates and activates Akt ("Characterization of a 3-phosphoinositide-dependent protein kinase which phosphorylates and activates protein kinase Ba"; Alessi et al., Curr. BioL, 7:261–269 (1997)), ("Dual role of Phosphatidylinositol 3,4, 5-triphosphate in the activation of protein kinase B"; Stokoe et al., *Science*, 277:567–570 (1997)). Akt is a proto-oncogene that inhibits apoptosis by phosphorylating Bad, thus, promoting its binding to, and blocking the activity of the cell survival factor Bcl-x ("A bad kinase makes good"; Franke et al.; *Nature*, 390:116–124 (1997)).

Accordingly, the inhibition of Akt activation potentiates cancer cell apoptosis. Translocation of PtdIns-PLCγ to the plasma membrane brings it into contact with its substrate $PtdIns(4,5)P_2$ resulting in more efficient hydrolysis to Ins $(1,4,5)P_3$ and diacylglycerol. The binding of $PtdIns(3,4,5)P_3$ to the SH2 domain of PtdIns-PLCγ, as well as the better recognized SH2 binding to tyrosine phosphate residues on autophosphorylated growth factor receptors, provides additional mechanisms for translocating PtdIns-PLCγ to the plasma membrane (Id.). An increase in intracellular free $Ca^{2+}$ caused by the release of intracellular stores of $Ca^{2+}$ by $Ins(1,4,5)P_3$ together with the activation of protein kinase C by diacylglycerol leads to a series of events that culminate in increased cell proliferation. PKC-ζ is also directly activated by $PtdIns(3,4,5)P_3$ (Activation of zeta isozyme of protein kinase C by phosphatidylinositol 3,4,5-triphosphate; Nakanishi et al.; *J. Biol. Chem.*, 268:13–16 (1993)). Thus, an increase in PtdIns-3-phosphates in the cell membrane results in the activation of two different pathways, one leading to increased cell proliferation, the other to inhibition of cell death. These separate pathways explain the growth stimulating and transformation related effects of PtdIns-3-kinase.

Design Of PtdIns-3-Kinase Anti-Metabolites

As disclosed supra, the focus of the subject invention is to produce by rational methods antagonists of PtdIns-3-kinase metabolites. In order do so, the present inventors have elected to rationally designs antagonists of PtdIns-3-kinase metabolites such as PtdIns-3-phosphates, by utilizing the structure of the PtdIns-3-kinase substrate as a starting structure for modification. In particular, different modifications to this starting structure are judiciously selected and the effects thereof on activity evaluated, so that ideally an effective antagonist is produced. One method for obtaining effective antagonists is to maintain a high structural similarity between the antagonist and the substrate. That is, the modification is based on a balance between the new features providing the desired antagonistic effect and maintaining sufficient structural similarity such that metabolites are not produced. These antagonists will advantageously be sufficiently similar in structure to the metabolites such that they effectively interfere with the processing of the metabolites in the signaling cycle, down stream of the PtdIns-3-kinase step. Effective antagonists should have sufficient structural similarity to these metabolites so that they effectively compete with the metabolites for interaction with sites available for the step following phosphorylation by PtdIns-3-kinase, while at the same time being unaffected by this interaction. This should block the signaling cycle both upstream and downstream of the PtdIns-3-kinase mediated phosphorylation.

Figure 2:
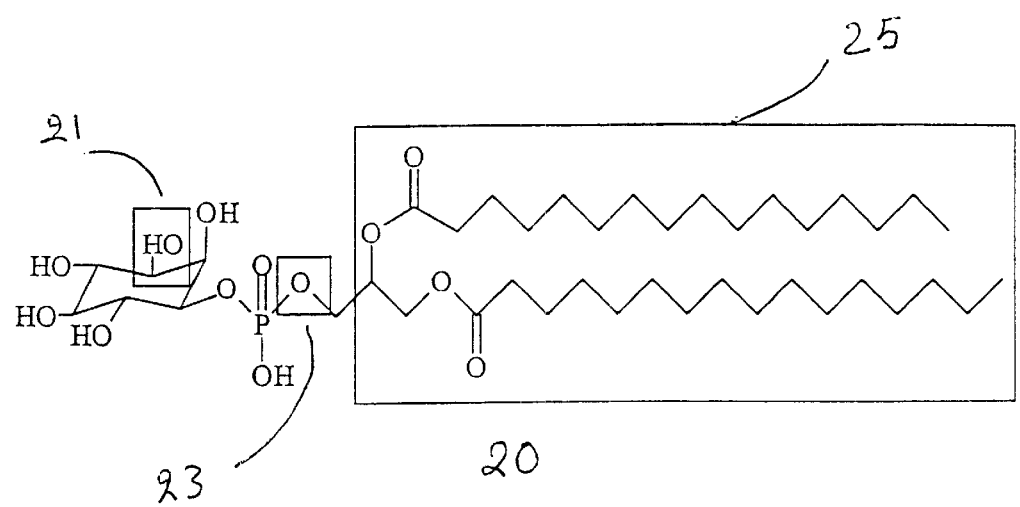
FIG. 2 is a schematic diagram of phosphatidylinositol (PtdIns)

The starting structure of the modified metabolite phosphatidylinositol (PtdIns) is contained in FIG. 2. As explained, PtdIns 20 is utilized as the starting structure for designing PtdIns-3-kinase cell growth signaling antagonists. More specifically, the present inventors elected to focus on three specific sites in the PtdIns structure as candidates to be modified in order to obtain analogs of PtdIns-3-kinase metabolites which function as effective antagonists. Ideally, such antagonists will exhibit the desired pharmaceutical properties in vivo and will selectively antagonize myo-inositol metabolites produced by PtdIns-3-kinase while not disrupting other cell signaling pathways, in particular of normal cells. The rationale for selecting these specific modifications is based on the present inventors' analysis and understanding of the chemistry associated with cell growth signaling.

A) The 3 Position of the myo Inositol Ring

The first position selected for modification was the 3 position of the myo-inositol ring. This was selected because analogs of myo-inositol in which the 3-hydroxyl group is removed or replaced can not be phosphorylated by PtdIns-3-kinase and appear to act as inhibitors of PtdIns-3-kinase signaling. D-3-deoxy-substituted myo-inositols are taken up by the myo-inositol transporter of cells and incorporated into cellular PtdIns by PtdIns synthetase leading to the selective growth inhibition of (some) transformed relative to normal cells. However, the affinity of the D-3-deoxy-substituted myo-inositols for uptake and PtdIns synthesis is less than that of myo-inositol itself and at physiological concentrations myo-inositol inhibits their growth inhibitory activity. D-3-deoxysubstituted PtdIns inhibits the growth of cancer cells in the presence of myo-inositol. In fact, D-3-deoxy-PtdIns and a more active analog have been reported to exhibit anti-tumor activity against human tumor xenografts in SCID mice ("Synthesis and Biology of 1D-3-Deoxyphosphatidylinisitol: A Putative Anti-metabolite of phosphatidylinositol-3-phosphate and an Inhibitor of Cancer Cell Colony Formation", Kozikowski, A. P. et al. *J. of Medicinal Chem.*, Vol.38, 7:1053–1056 (1995)), the contents of which are hereby incorporated by reference. Also, treatment of NIH 3T3 cells with D-3-deoxy-PtdIns blocks the activation of Akt due to inhibition of PH domain binding. Moreover, D-3deoxy myo-inositols kill cells by inducing apoptosis which is consistent with the role of PtdIns-3-kiriase and Akt in preventing apoptosis (Id.).

The position for a first modification, site 21, corresponds to the 3 position on the inositol ring. As discussed above, PtdIns-3-kinase phosphorylates the D-3-OH position of the myo inositol ring. Modifying the 3 position of the inositol ring to preclude phosphorylation should interrupt the PtdIns-3-kinase signaling cycle. Precluding phosphorylation by PtdIns-3-kinase is achieved by removing the oxy group at the 3 position of the inositol ring.

Figure 3:
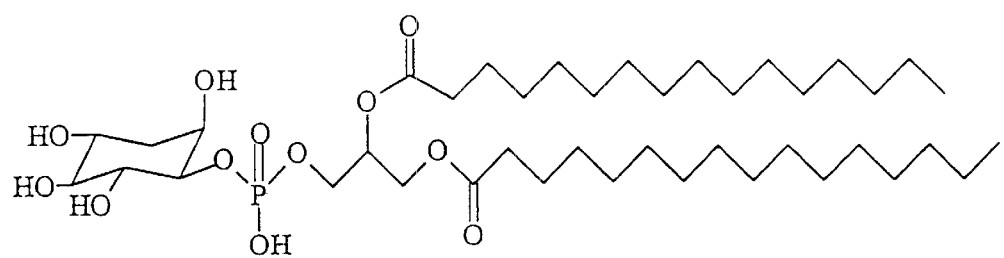
FIG. 3 shows the structure of 3-deoxy-phosphatidyl-myo-inositol (30) (DPI)

The resultant modified structure, 3-deoxy-phosphatidyl-myo-inositol 30 (DPI) is contained in FIG. 3. In fact, DPI is recalcitrant to phosphorylation by PtdIns-3-kinase and therefore possesses cell growth inhibiting activity. Assays of the biological activity of DPI show that the compound inhibits colony formation by HT-29 human colon carcinoma cells. DPI exhibits an $IC_{50}$ of 35 $\mu$M (Id.).

Also, it has been demonstrated by the inventors that the 3 position of the myo-inositol ring can be modified to include non-phosphorylable substituents. In particular, the 3 position hydrogen atom in DPI can be substituted by a halogen, such as fluorine or chlorine. The synthesis and biological activity of such substituted DPI analogs is the subject of U.S. Pat. No. 5,227,508, the contents of which are hereby incorporated in their entirety. For example, it has been shown that the PtdIns analog bearing a fluorine atom in place of the 3-hydroxy group inhibits colony formation by HT-29 human colon carcinoma cells with an $IC_{50}$ of 37 $\mu$M.

B) The DAG sn-3 Oxygen Position

A second site selected by the inventors for the rational drug design of PtdIns antagonists is the sn-3 oxygen of the DAG. This was chosen because in the PtdIns signaling cycle, PtdIns-3-kinase metabolites are hydrolyzed by PI-PLC at the sn-3 oxo position. Therefore, precluding hydrolysis by substituting the sn-3 oxygen by a non hydrolyzable group should allow the concentration of PtdIns-3-kinase anti-metabolites to remain at a high level, thereby inhibiting PtdIns-3-kinase activity.

More specifically, the present inventors elected to modify the 3-sn oxygen position of the PtdIns analog, preferably to preclude hydrolysis by PI-PLC, by replacing the oxygen with a methylene group ($CH_2$). This modification was made because it is hypothesized that maintaining a high concentration of PtdIns-3-kinase anti-metabolites requires that such metabolites be present in the environment of PtdIns-3-kinase. Moreover, it is believed that the low potency of these compounds may be due to their hydrolysis by phospholipases including PI-PLC. Also, DAG produced by hydrolysis can activate PKC, which may lead to tumor cell proliferation. By contrast, the present inventors seek to obtain novel antagonists which act as PtdIns-3-kinase anti-metabolites which are not hydrolyzable at the 3-sn oxygen by PI-PLC. These antagonists are designed based on a double modification of the starting structure. In particular, both the 3 position 21 of the myo-inositol ring and the sn-3 oxygen position 23 of the DAG were modified.

Figure 4:
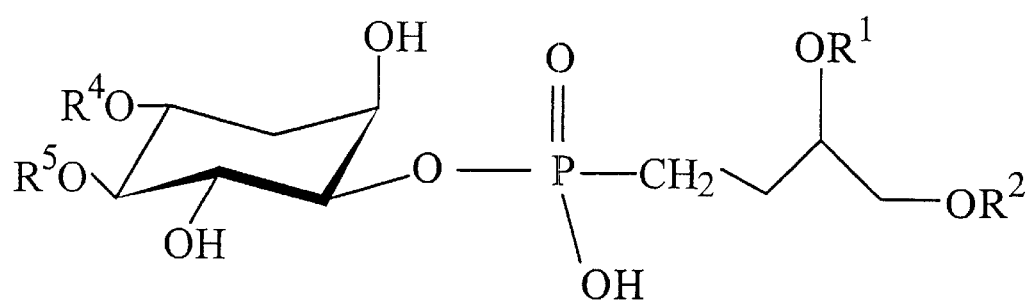
FIG. 4 shows the generic structure of phosphonate analogs of DPI (30)
Figure 5:
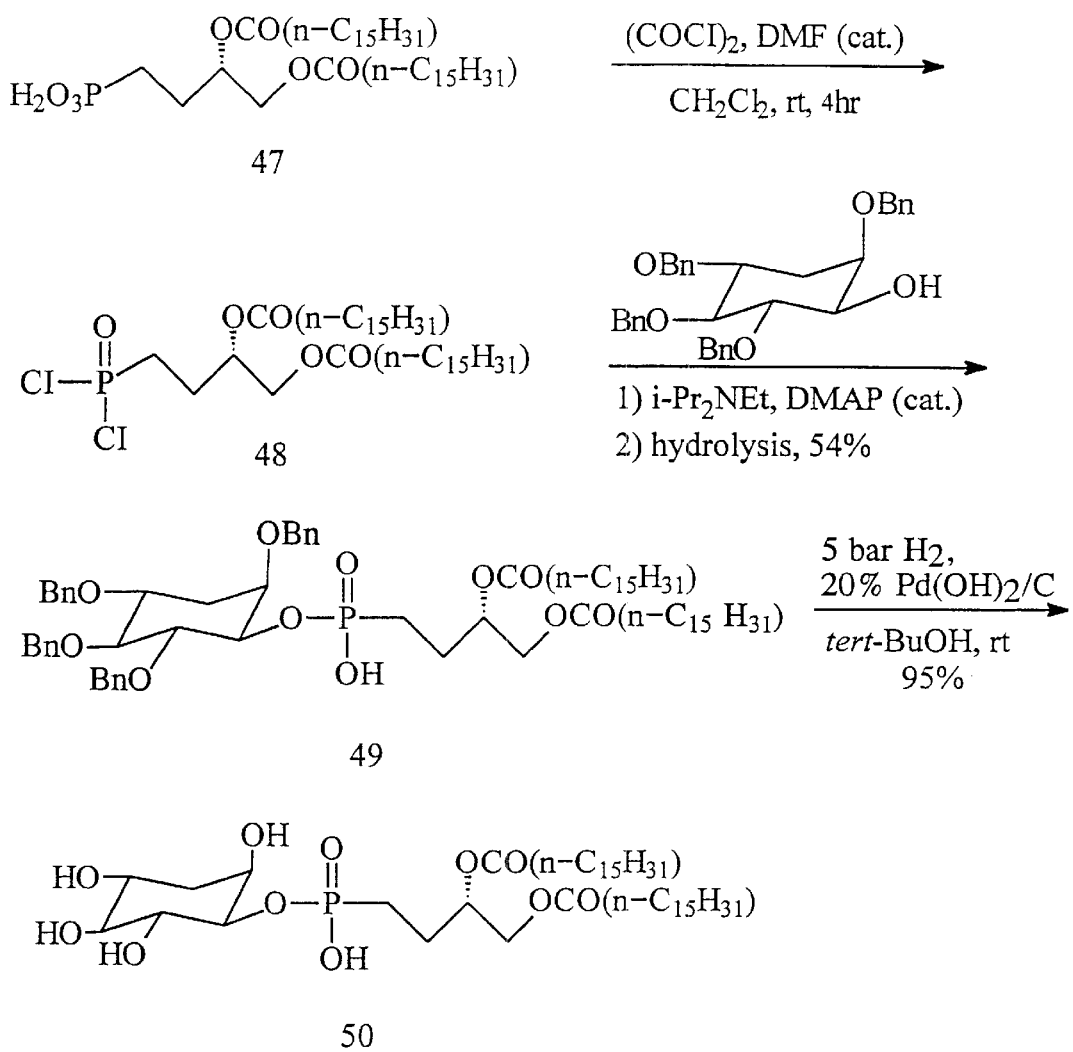
FIG. 5 is a schematic diagram of the synthesis of the 3-deoxy-phosphatidyl-myo-inositol phosphonate analog (50)

FIG. 4 shows the generic structure of phosphonate analogs of DPI. Also, the synthesis of the 3-deoxy-phosphatidyl-myo-inositol phosphonate analog 1-O-[(3S)-3, 4-bis(palmitoyloxy)butylphosphonyl]-1D-3-deoxy-myo-inositol (50) is schematically outlined in FIG. 5. For the synthesis of the phosphonate analog (50), the dichloride (48) is prepared from (S)-3,4-bis(palmitolyloxy)butyl-hosphonic acid (47) with oxalyl chloride in the presence of a catalytic amount of DMF at room temperature. The inositol component, ID-2,4,5,6-tetra-O-benzyl-3-deoxy-myo-inositol (49) is obtained as reported before. Phosphorylation of (49) with (48) in the presence of a base provides monoesterchloride intermediate which is transformed into (40) by hydrolysis, a reaction which proceeds in a surprisingly sluggish manner. After purification by preparative TLC, catalytic hydrogenation of (40) using $Pd(OH)_2/C$ in tert-butanol provides the target phosphonate1-O-[(3S)-3,4-bis(palmitoyloxy)butyl-phosphonyl]-1D-3-deoxy-myo-inositol (50) in good yield.

C) The Diacylglycerol Position

A third site of interest for rational drug design of PtdIns antagonists selected by the inventors was the diacylglycerol at position 25 (the lipid ester moiety in the DAG). The diacylglycerol position was selected for modification in order to potentially enhance the PtdIns-3-kinase anti-metabolite properties of the compounds designed according to the invention.

Specifically, rational modification of the diacylglycerol ester lipid at position 25 was effected by substituting the diacylglycerol group with a lipid moiety of a compound having known PtdIns-3-kinase inhibition properties and/or anti-tumor properties. It is noted that diacylglycerol, which is an endogenous activator of PKC and tumor cell growth, and which is liberated upon PtdIns analog hydrolysis, has antagonizing effects against the inhibition of PtdIns-3-kinase signaling. By contrast, the lipid moiety which was incorporated in the designed compounds lacks the antagonist effects of diacylglycerol against PtdIns-3-kinase signaling inhibition.

Thus, novel compounds were designed potentially to increase the potency of D-3 deoxyPtdIns and to reduce the possibility of unwanted side effects stemming from the metabolic production of diacylglycerol.

Figure 6:
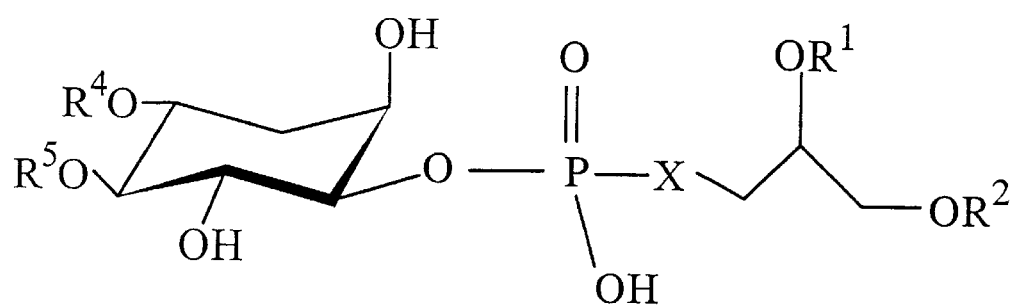
FIG. 6 shows a generic structure of D-3-deoxyPtdIns ether lipid analogs designed according to the invention.

FIG. 6 shows a generic structure of D-3-deoxyPtdIns ether lipid analogs designed according to the invention. Design of 3-deoxy-PI ether lipid analogs is of especial interest because of the potential enhanced stability of these compounds to phospholipases. This will potentially occur because the 3-deoxy-PI ether lipid should not function as a substrate for PI-PLC. A further advantage of the ether lipids is that they have previously been shown to possess intrinsic anti-tumor activity against a variety of tumor types. In fact, some ether lipid analogs which have undergone clinical testing as anti-tumor agents are inhibitors of PI-3-kinase. They affect several aspects of lipid intracellular signaling, and their anti-tumor activity may arise, from a combination of effects on the signaling pathway. In this regard, 1-O-octadecyl-2-O-methylglycero-phosphocholine (edelfosfine) and a number of related compounds are known inhibitors of PI-PLC with $IC_{50}$s in the low $\mu$M range.

Figure 7:
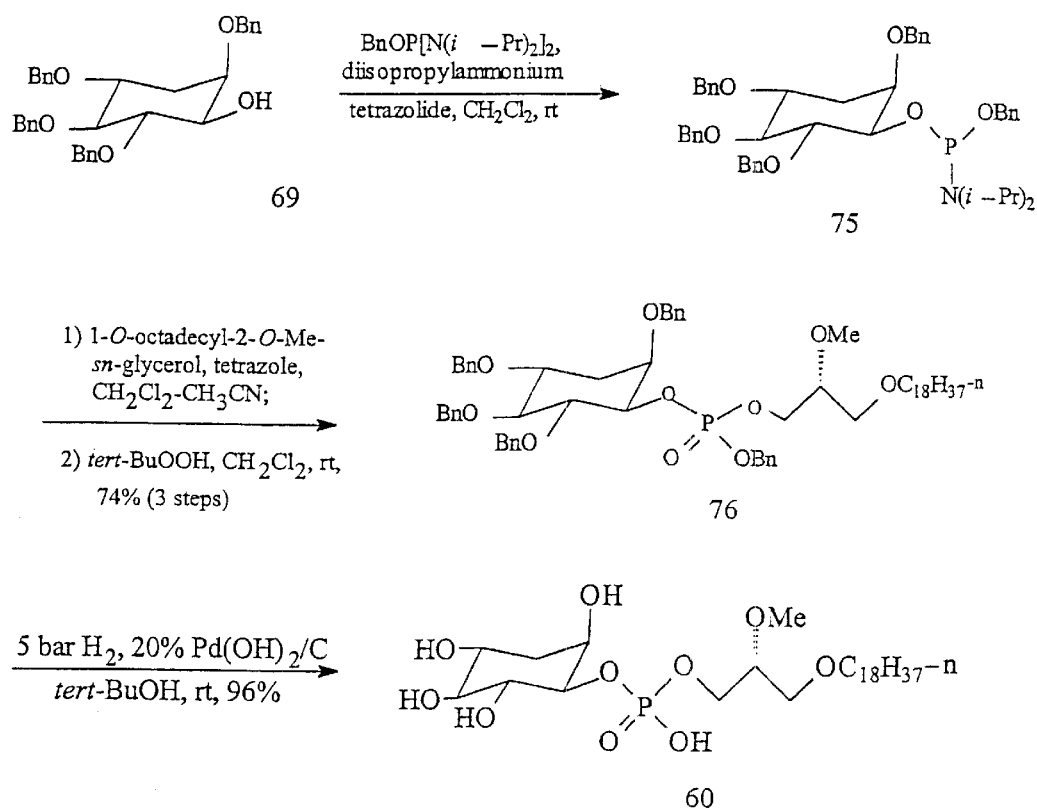
FIG. 7 is a schematic diagram of the synthesis of OMDPI (60)

In particular, the compound 1-O-(2-O-methyl-1-O-octadecyl-sn-glycero-3-phospho)1D-3-deoxy-myo-inositol (OMDPI) was synthesized by modifying DPI to replace the dipalmitoylglycerol group with 1-O-octadecyl-2-O-methyl-sn-glycerol. The synthesis of OMDPI (60) is schematically outlined in FIG. 7.

The starting material for the D-3-deoxy-PtdIns ether lipid analog is the regioisomeric mixture of vibumitol (i.e., 3-deoxy-myo-inositol) 1,2:4,5- and 1,2:5,6-diacetonides (62), (63), obtained from L-quebrachitol. Controlled acidic hydrolysis of the more labile trans acetonide moieties in this mixture provides monoacetonide (64) in 79% yield. All of the three required O-benzyl groups are then introduced simultaneously with benzyl bromide and NaH in DMF (74% yield), and the remaining cis-acetonide gas removed by acidic hydrolysis (96% yield). The resulting diol (66) is protected selectively at the equatorial 1-hydroxyl by reacting its cyclic dibutylstannylene derivative with chloromethyl methyl ether. Following benzylation of the 2-hydroxyl (73% yield) and acidic hydrolysis of the MOM ether (77% yield) resulted in the formation of the key intermediate, 2, 4, S, 6-tetra-O-benzylburnitol (69), in crystalline form.

Figure 8:
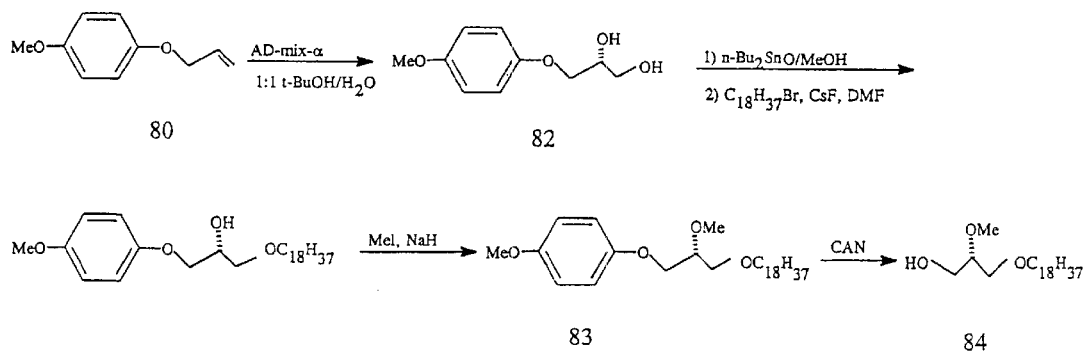
FIG. 8 illustrates the synthesis of 1-O-octadecyl-2-O-Me-sn-glycerol (84)

Another component for the synthesis of 3-deoxy-phosphatidylinositol ether lipid analog is 1,2 disubstituted-sn-glycerol, which is obtained in high yield and in high enantiomeric excess by carrying out the asymmetric dihydroxylation of allyl 4-methoxyphenyl ether (80). 1-O-octadecyl-2-O-Me-sn-glycerol (84) is illustrated in FIG. 8 as an example. Selective monoalkylation with 1bromooctadecane is achieved via the 1-2-O-stannylene intermediate, and the resulting secondary alcohol (82) is then methylated to provide (83). This particular strategy allows facile manipulation of the size of the alkyl side chains, a feature which was found to significantly affect the solubility of the resultant PtdIns analogs under the assay conditions. Final removal of the 3-O-(4-methoxyphenyl) group with ceric ammonium nitrate (CAN) provides the desired glycerol (84).

Subsequently phosphitylation of intermediates (69) with O-benzyl N,N,N'N'-tetraisopropyl-phosphorodiamidite catalyzed by diisopropylammonium tetrazolide provided the phosphoramidite (75) in quantitative yield which was then coupled with ether lipid (84) in the presence of tetrazole. The resulting phosphates were oxidized to the phosphates (76) with tert-butyl hydroperoxide (74% yield for 3 steps). Final hydrogenolysis then provides the desired ether lipid analog 1-O-(2-O-methyl-1-O-octadecyl-sn-glycero-3-phospho)-1D-3-deoxy-myo-inositol (60) in 96% yield.

Figure 9:
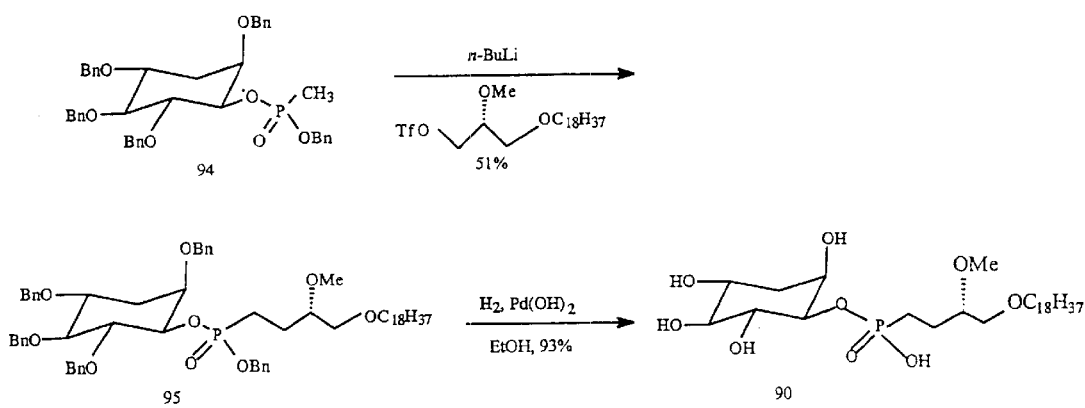
FIG. 9 is a schematic outline of the synthesis of the phosphonate analog (90) of OMDPI.

The synthesis of the phosphonate analog 1-O-[(3S)-methoxy-4-(octadecyloxy)butylphosphonyl]-1D-3-deoxy-myo-inositol (90) of OMDPI is schematically outlined in FIG. 9. Methyl phosphonate (94) underwent an $S_N2$ reaction with glyceryl triflate to yield the phosphonate (95). Lastly, hydrogenation of (95) delivered (90).

Biological Activity

To confirm the efficacy of the subject analogs in inhibiting PtdIns-3-Kinase, and in particular the inhibition of cell proliferation and/or differentiation and/or induction of apoptosis of cancer cells, the following experiments were controlled. These experiments were effected in particular to assess the anti-tumor activity and the binding properties of compounds according to the invention.

A) Anti-tumor Activity

Specifically, anti-tumor activity was assessed by growing HT-29 colon cancer cells colonies in soft agarose which were then exposed to compounds according to the invention for 7 days and the colonies then counted. Values were expressed as the $IC_{50}$ for inhibition of colony formation and are the mean of 3 determinations±S.E. The results of these experiments are contained in Table 1 below.

TABLE 1

| In Vitro Anti-Tumor Activity | |
|---|---|
| Compound | Soft Agarose $IC_{50}$ ($\mu$M) |
| 3-deoxy-PtdIns (30) | 35 ± 9 |
| 3-flouro-PtdIns (35) | 37 ± 3 |
| 2,3-dideoxy-PtdIns | 50 ± 7 |
| 3-deoxy-PtdIns phosphonate (50) | 10 ± 2 |
| OMDPI (60) | 2.1 ± 0.1 |
| OMDPI phosphonate (90) | 45 ± 7 |

As shown in Table 1, 3-deoxy-PtdIns (30) and 3-Fluoro-3-deoxy-PtdIns (35) inhibited colony formation of HT-29 human colon carcinoma cells with $IC_{50}$ values of 35 and 37 $\mu$M, respectively, while 3-chloro-3-deoxy-PtdIns (not shown) was virtually inactive (<20% growth inhibition at maximum tested concentration). The ether lipid analog OMDPI (60) was found to be 15-fold more active in its growth inhibitory activity (2 $\mu$M) compared to DPI. Replacement of the phosphate group of DPI by a phosphonate was found to increase the growth inhibition by over a 3-fold ($1C_{50}$ for (50) is 10 $\mu$M). However, the same modification decreased the activity of OMDPI ($IC_{50}$ for (90) is 45 $\mu$M).

These results indicate that replacement of the diacylglycerol moiety with an ether 20 lipid group resulted in an over 15-fold increase in growth inhibition activity (compare compounds (30) and (60)). Replacement of phosphate by phosphonate increased the growth inhibiting activity of 3-deoxy-PI by almost 3-fold (compare compounds (30) and (50)). However, it decreased the growth inhibiting activity of the 3-deoxy ether lipid analog (compare (60) and (90)).

Based on the observation that replacement of the diacylglycerol moiety of D-3-deoxy-PtdIns with ether lipid provided over 15-fold increase in in vitro growth inhibitory potency against HT-29 tumor cells, the activity of 1-O-octadecyl-2-O-methyl-sn-glycero3-phospho-myo-inositol (that is the ether lipid analog of PtdIns with a myo-inositol group instead of a D-3-deoxymyo-inositol group) was then tested. 1-O-octadecyl-2-O-methyl-sn-glycero-3-phospho-myo-inositol was found to be a poor inhibitor of PtdIns-PLC and only a weak inhibitor of cancer cell growth. Based on these results, it appears that the increase in anti-tumor activity of OMDPI is not solely attributable to the incorporation of the ether lipid moiety. Rather, the enhanced anti-tumor activity of OMDPI apparently is the synergistic result of both the modification of the 3 position of the myo-inositol ring 21 and the diacylglycero position 25.

B) PH Domain Inhibition

Figure 10:
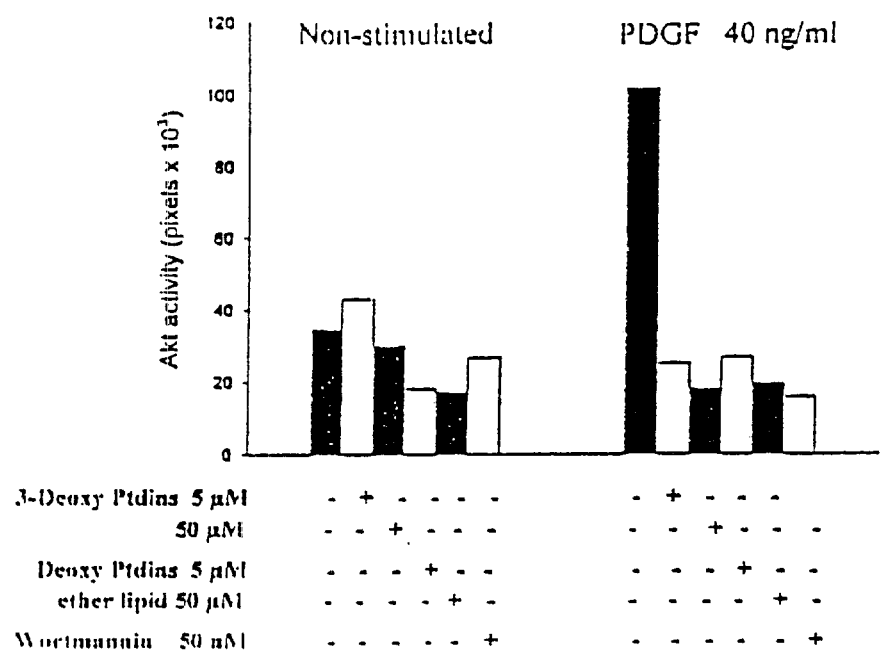
FIG. 10 shows the results for PH Domain inhibition.

PtdIns-3-phosphates bind to and activate PH domain containing enzymes. Accordingly, the ability of the D-3-deoxy-PtdIns analogs to inhibit the activation of the PH domain dependent enzyme Akt was investigated. NIH 3T3 cells were transiently transfected with human Akt with a hemagglutinin (HA) epitope tag. The cells were exposed to the D-3-deoxy-PtdIns analogs for 6 hours and stimulated with PDGF to activate Akt. The Akt was immunoprecipitated with anti-HA antibody and its ability to phosphorylate histone-H2B measured using [$\gamma^{32}$P]-ATP. Histone H2B was separated by SDS PAGE and bands on the gel quantitated using a phosphorimager. The results are shown in FIG. 10. PDGF resulted in a marked increase in Akt activity in the cells and both D-3-deoxy-PtdIns and D-3-deoxy-PtdIns ether lipid blocked Akt activation. Wortmannin, an inhibitor of PtdIns-3-kinase, blocked Akt activation as expected.

Also, the in vitro inhibition of bovine PI-PLC and of bovine brain p110/p85 PI-3-kinase were measured as previously described ("In vitro and in vivo activity of the phosphatidylinositol-3-kinase inhibitor, wortmannin"; Schultz et al.; *Anticancer Res.*, 15:1135–1140 (1995)). The results of this binding experiment are summarized in Table 2:

TABLE 2

|  | -PH Domain Inhibition | |
| --- | --- | --- |
|  | PtdIns-PLC IC50 W) | PI-3-K IC50 (gM) |
| (30) | N/A | >250 |
| (35) | 8 | 30 |
| (50) | N/A | N/A |
| (60) | 19.9 | 2.5 |
| (90) | 10 | 5.3 |

N/A = not active, with <20% inhibition at 100 gM.

The results show that all the compounds are only weak inhibitors of PI-PLC compared to 1-O-octadecyl-2-O-methyl glycerophosphocholine which has an $IC_{50}$ under the same assay conditions of around 1 $\mu$M. However, the 3-deoxy ether lipid PIs are relatively potent inhibitors of PI-3-kinase with $IC_{50}$ values of 2 to 5 $\mu$M. 1-O-octadecyl-2-O-methylglycerophosphocholine has previously been found to be an inhibitor of PI-3kinase with an $IC_{50}$ of 35 $\mu$M, while the mylo-inositol containing analog is a much weaker inhibitor with an $IC_{50}$ of 90 $\mu$M. Thus, the presence of a 3-deoxy-myo-inositol moiety appears to impart PI-3-kinase inhibiting activity to the compounds.

Based on the unexpectedly low anti-tumor and PI-3-kinase inhibition $IC_{50}$ values obtained with the lead compound OMDPI, in vivo and human clinical tests are being designed to establish anticancer protocols based on OMDPI.

Example 1 illustrates the synthesis of compounds (50), (60) and (90). Example 2 shows in vivo activity and toxicity studies comparing OMDPI (60) and DPI (30) as anti-tumor agents.

EXAMPLE 1

Preparation of Compound 50

To a suspension of 110 mg (170 gmol) of (47) in 2 mL of $CH_2Cl_2$, and 5 $\mu$L of DMF under $N_2$, was added 119 $\mu$L (1.36 mmol) of oxalyl chloride. The white solid disappeared in five minutes, the resulting solution is then stirred at room temperature for another 4 hours. After removal of the solvent in vacuum, the residue (compound (48)) is dried and used directly in the next step without further purification.

To a solution of (48) and 89 mg (170 $\mu$mol) of (49) in 2 mL of $CH_2Cl_2$, was added 89 $\mu$L (0.51 mmol) of i-$pr_2$NEt and 5 mg of DMAP. The resulting mixture was allowed to stir at room temperature overnight followed by hydrolysis with water. The product was then extracted with $CDCl_3$ and dried over $MgSO_4$. After concentration, the residue was purified by preparative TLC developed by $CH_2Cl_2$/MeOH (v/v 9/1), giving 105 mg (54%) of (40) as a yellow syrup.

99.1 mg of (40) in 11 mL of tert-butanol is hydrogenated under 5 bar $H_2$ over 56 mg of 20% Pd(OH)$_2$/C for 12 hours. After filtration, the filtrate is concentrated and dried in vacuum, leaving 64.9 mg (95%) of 1-O-[(3S)-3,4-bis(palmitoyloxy)butylphosphonyl]-1D-3-deoxy-myo-inositol (50) as a white solid.

Preparation of Compound 60

A solution containing 1.80 g (1.74 mmol) of (69) in 50 ML of tert-butanol was hydrogenated in a Parr shaker under 70 psi of $H_2$ for 36h, using 1.0 g of 20% Pd(OH)$_2$/C (Aldrich, 50% $H_2$0) as catalyst. The catalyst was filtered out and the filter cake was washed with 100 ml of MeOH/CHCl$_3$ (v/v=1/1). The filtrate was concentrated and dried in vacuo leaving 0.98 g (96%) of (60) as a white powder.

Preparation of Compound 90

To a solution of 262 mg (0.5 mmol) of (99), 113 mg (0.6 mmol) of ammonium O-benzyl-H-phosphonate, 0.2 mL of pyridine in 2 mL of $CH_2Cl_2$, was added 74 $\mu$L (0.6 mmol) of pivaloyl chloride. The mixture was stirred at room temperature for 10 minutes, then diluted with 50 mL of EtOAc. The organic layer was washed with 10 mL×2 saturated aqueous CUS04, dried over MgS0$_4$. After evaporation, the residue was purified by column chromatography on silica gel with EtOAc/hexane 1:1, affording 335 mg (94%) of (93) as a colorless oil.

Under $N_2$, to a solution of 170 mg (0.25 mmol) of (93) and 20 mg (60%, 0.5 mmol) of NaH in 2 mL anhydrous THF, is added 31 $\mu$L (0.5 mmol) of MeI. The resulting mixture was allowed to stir at room temperature overnight and then partitioned in 50 mL of EtOAc and 5 mL of $H_2$0. The organic layer was washed with brine and dried over MgS0$_4$. After evaporation, the residue was purified by column chromatography on silica gel with EtOAc/hexane 2:1, giving 112 mg (65%) of (94) as a colorless oil.

Under $N_2$, to a solution of 77 mg (0.11 mmol) of (94) in 2 mL of anhydrous THF at −78° C., is added 56 $\mu$L (0.11 mmol, 2.0 N in Hexane) of n-BuLi. After stirring at −78° C. for 30 min., a solution of triflate in 1 mL of THF was dropped in. The resulting reaction mixture was warmed to room temperature slowly and stirred overnight. 1 mL of MeOH was added, and the reaction mixture was then concentrated. After column chromatography on silica gel with EtOAc/hexane 1/1, 57.9 mg (51%) of (95) is obtained as a colorless oil.

A solution of 49 mg (47 $\mu$mol) of (95) in 3 mL of EtOH was hydrogenated over 25 mg of 20% Pd(OH)$_2$/C under atm. of $H_2$ at room temperature for 20 hours. After filtration, the filter cake was washed with 20 mL of CHCl$_3$/MeOH (v/v=1/1). Evaporation and drying in vacuo left 25.7 mg (93%) of 1-O-[(3S)-methoxy-4-(octadecyloxy)butylphosphonyl]-1D-3-deoxy-myo-inositol (90) as a white powder.

In Vivo Activity of DPI and OMDPI

Preliminary studies of in vivo anti-tumor activity were conducted in SCID (severe combined immunodeficient) mice implanted subcutaneously with 10 HT-29 human colon adenocarcinoma cells. Injection of compounds (30) and (60) was begun 4 days after tumor inoculation in groups of 8 mice as 4 daily intraperitoneal injections of the compounds suspended in 3% EtOH, 3% Tween 20, 0.9% NaCl. Tumor volume was measured with calipers on day 10. AS shown in Table 3, compound (30) was lethal at a 5 daily dose of 500 mg/kg and exhibited no anti-tumor activity at half this dose. Compound (60) was not toxic at the highest dose tested of 150 mg/kg per day and inhibited tumor growth by 67%. However, at doses of 100 and 50 mg/kg per day, the compound did not elicit anti-tumor activity.

$10^7$ tumor cells were injected s.c. on day 0. Palpable tumor was detected on day 4 with a mean volume of 0.009 cm$_3$. Drugs were injected i.p. suspended in sterile 3% ethanol, 0.1% Tween 20, and 0.9 NaCl.

TABLE 3

Anti-Tumor Activity Against Established
HT-29 Human Colon Cancer in SCID

| Compound Dose (mg/kg) | Schedule[a] | Tumor volume[b] on day 10 (cm³) | T/C % | P[c] |
|---|---|---|---|---|
| Control (30) | | 0.27 ± 0.04 | | |
| 500 | i.p., qd 4–5 | lethal | | |
| 250 (60) | i.p., qd 4–7 | 0.30 ± 0.06 | 111.1 | NS |
| 150 | i.p., qd 4–7 | 0.09 ± 0.07 | 33.3 | <0.05 |
| 100 | i.p., qd 4–7 | 0.32 ± 0.09 | 118.0 | NS |
| 50 | i.p., qd 4–7 | 0.258 ± 0.05 | 103.7 | NS |

[a] e.g. 250 mg.kg i.p., qd 4–7 means that the 250 mg/kg does is given as an intraperitoneal injection each day from days 4 to 7 (four daily injections) after the tumors are implanted.
[b] Tumor volume values are the mean for 8 mice per group with S.E.
[c] The P column is the significance value for Student's test comparing the tumor volumes in the treated group to the tumor volumes in the control group. 0.05 is usually the maximum value for significance. NS is 'not significant', meaning that these studies are not repeated.

Therefore, based on these results, OMDPI exhibited significant in vivo anti-tumor 20 activity against both established human MCF-7 breast cancer and established HT-29 colon tumor xenografts implanted in SCID mice. OMDPI administered by a 4 or 5 day daily i.p. schedule resulted in a 60% inhibition of the growth of MCF-7 breast cancer and a 67% inhibition of the growth of HT-29 colon cancer xenografts. The activity of OMDPI administered by a 10 day schedule provides 80% inhibition of the growth of MCF-7 breast cancer xenografts.

Figure 11:
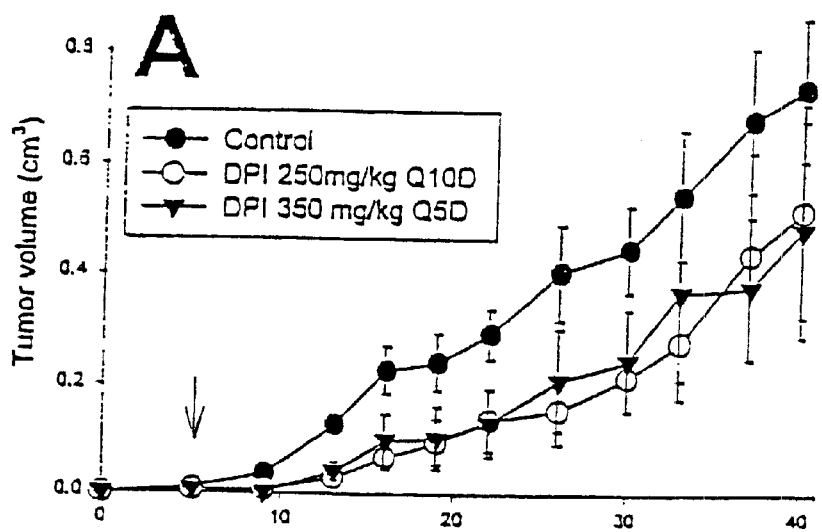
FIGS. 11 and 12 show the cell growth inhibiting ability of DPI (30) and OMDPI (60), respectively.
Figure 12:
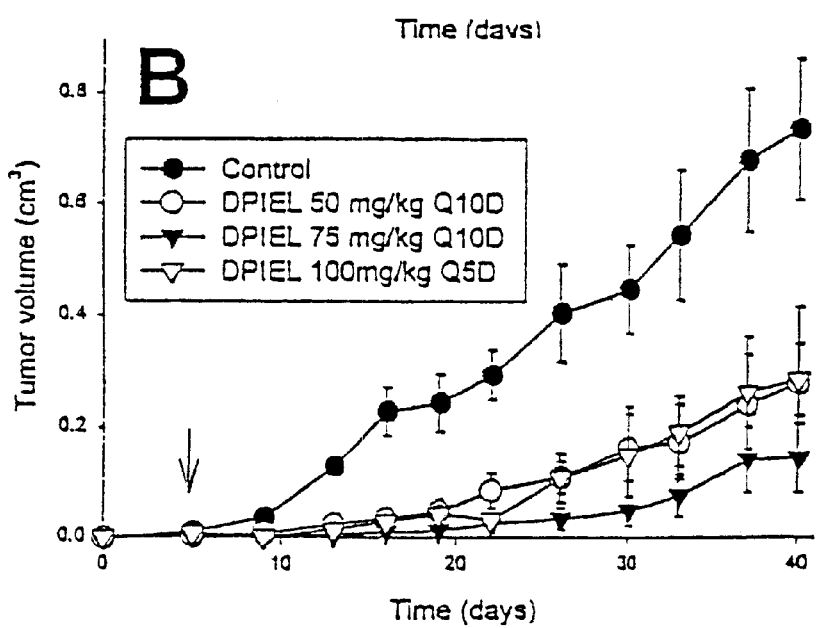

Also, the relative ability of D-3-deoxy-PtdIns and OMDPI, when administered i.p. as a daily micellar suspension to inhibit the growth of MCF-7 human breast cancer xenografts in SCID mice, was further evaluated. These results are contained in FIGS. 11 and 12. Based on these results, it can be seen that D-3-deoxy-PtdIns exhibits only moderate anti-tumor activity (T/C 62%, p<0.05). More specifically, OMDPI exhibited good anti-tumor activity when administered for 10 days at a dose of 75 mg/kg (T/C 20%, p<0.05) and slightly less activity when administered for 5 days at 100 mg/kg (T/C 39%, p<0.05). These were the maximum tolerated doses that could be given by these schedules. Not shown are the effects of cyclophosphamide 265 mg/kg which was administered on day 5 as a positive control and which resulted in a 43% inhibition of the growth of MCF-7 xenografts. The results of these experiments demonstrate OMDPI has significant antitumor activity (T/C 20%) against a relatively chemotherapy resistant human tumor xenograft (MCF-7 breast cancer) when administered over 10 days.

Preliminary Toxicology Tests Comparing DPI (30) and OMDPI (60)

In order to evaluate clinical safety, toxicity tests were conducted by administering DPI or OMDPI to groups of 4 male BALB/C mice daily by i.p. injection for 5 days at the maximum tolerated dose. These results are contained in Table 4. As shown therein, OMDPI had no effect on body weight or platelet count and did not result in elevation of serum liver or kidney enzymes. Moreover, there was a 33% decrease in total white blood cell count. It should be noted, however, that this is not sufficient for a cytotoxic drug to be considered myelosuppresive. Thus, while the cause of death by OMDPI remains undetermined it is not liver or renal toxic and is only weakly myelosuppresive.

As discussed, Table 4 contains the toxicity results obtained with groups of 4 male BALB/C mice, which were administered the compounds daily by i.p. injection for 5 days at the doses shown and killed 24 hr after the last dose. Values are mean±S.E. The p values are shown only where there was a significant difference to control.

TABLE 4

Preliminary ToxicoLQU Studies of DPI and OMDPI in Mice

| Compound | Weight Change % | White blood cells | Platelets × 10⁶ | BUN | Total Protein | ALT |
|---|---|---|---|---|---|---|
| Control | +6.6 ± 1.9 | 8.7 ± 0.7 | 1.1 ± 0.1 | 20.5 ± 1.5 | 5.4 ± 0.2 | 34.5 ± 2.7 |
| deoxy-PtdIns 300 mg/kg | −4.3 ± 1.9 p < 0.05 | 7.9 ± 0.5 | 0.9 ± 0.1 | 15.7 ± 0.5 | 4.6 ± 0.1 | 30.5 ± 4.6 |
| deoxy-PtdIns Ether Lipid 100 mg/kg | +2.3 ± 1.5 p < 0.05 | 5.8 ± 0.3 p < 0.05 | 0.9 ± 0.1 | 18.7 ± 1.0 | 4.9 ± 0.1 | 32.7 ± 2.4 |

Unlike D-3-deoxy-PtdIns, OMDPI exhibits good aqueous solubility, i.e., sufficient for a 10 mg/ml solution control in 0.1% Tween 20 to be used for intraperitoneal injection as an opalescent solution. Therefore, OMDPI should be readily formulated for intravenous use, should this be determined to be the optimal route for clinical administration. Also, it is believed that OMDPI should exhibit good anti-tumor activity and exhibit good bioavailability if orally administered. In this regard, it was noted that the ether lipids 1-O-octadecyl-2-O-methylglycero-phosphocholine (edelfosine) and hexadecylphosphocholine (mitelfosine) have shown clinical anti-tumor activity when administered orally as well as parenterally.

Based on this result, 1-O-(2-O-methyl-1-O-octadecyl-sn-glycero-3-phospho)-ID-3-deoxy-myo-inositol (OMDPI) is presently the lead compound of the invention for further development, essentially because of its superior activity relative to D-3-deoxy-PtdIns and also because of its increased aqueous solubility.

However, while OMDPI is currently the lead compound, the present invention is broadly directed to the identification of compounds that inhibit PtdIns-3-Kinase signaling. In the preferred embodiment, such compounds will be synthesized by modification of a PtdIns-3-Kinase substrate, most preferably phosphatidylinositol.

The design of such compounds is discussed above. In an especially preferred embodiment, these compounds will comprise 3-deoxy-D-myo-inositol analogs having the formula (I):

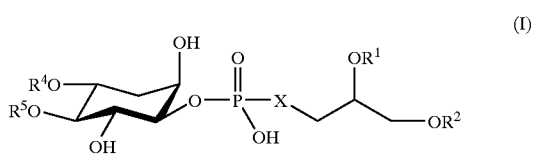

(I)

wherein X is O or $CH_2$; R an $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl or $(C9-C_{32})$ alkenylaryl, with the proviso that when X is O, $R^3$ is not $(C_{15})$ alkyl; $R^4$ and $R^5$ are individually hydrogen or a phosphate group; or when $R^4$ or $R^5$ is not hydrogen, a pharmaceutically acceptable salt thereof; or will comprise 3-deoxy-D-myo-inositol analogs having the formula (I1):

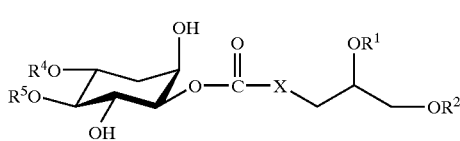

wherein X is O or $CH_2$; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl, $(C_9-C_{32})$ alkenylaryl or $C(O)R^3$; and $R^3$ is $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl or $(C_9-C_{32})$ alkenylaryl; $R^4$ and $R^5$ are individually hydrogen or a phosphate group; or when $R^4$ or $R^5$ is not hydrogen, a pharmaceutically acceptable salt thereof.

Based on the results obtained with the compounds synthesized to date, it is anticipated that these compounds will comprise significant therapeutic application. In particular, these compounds should inhibit PtdIns-3-Kinase signaling and the biological effects associated therewith. More specifically, these compounds should selectively inhibit PtdIns-3-Kinase cell proliferation and/or differentiation and/or promote apoptosis especially of cancer and other neoplastic cells.

Thus, the compounds produced according to the invention will be used to treat conditions wherein inhibition of PtdIns-3-Kinase signaling is therapeutically beneficial. This will include conditions that involve abnormal cell growth and/or differentiation such as cancers and other neoplastic conditions. Also, the subject compounds may be used to treat other conditions involving abnormal cell proliferation and/or differentiation such as dermatological conditions and disorders. Also, the subject compounds may be useful in treating inflammatory conditions such as arthritis, psoriasis, autoimmune disorders such as myasthenia gravis, lupus, multiple sclerosis, and others, and conditions involving abnormal platelet aggregation. The preferred indication is cancer, especially cancers involving over-expression of EGF and/or the PDGF receptor, cancers that express mutant ras, or cancers which comprise a Bcr/Abl translocation. Examples of cancers which may be treated according to the invention include colon, pancreatic, prostate, head and neck, gastric, renal, brain and CML.

The subject therapies will comprise administration of at least one compound according to the invention in an amount sufficient to elicit a therapeutic response, e.g., inhibition of tumor cell proliferation and/or differentiation and/or promotion of apoptosis.

The compound may be administered by any pharmaceutically acceptable means, by either systemic or local administration. Suitable modes of administration include oral, dermal , e.g., via transdermal patch, inhalation, via infusion, intranasal, rectal, vaginal, topical parenteral (e.g., via intraperitoneal, intravenous, intramuscular, subcutaneous, injection).

Typically, oral administration or administration via injection is preferred. The subject compounds may be administered in a single dosage or chronically dependent upon the particular disease, condition of patient, toxicity of compound, and whether this compound is being utilized alone or in combination with other therapies. Chronic or repeated administration will likely be preferred based on other chemotherapies.

The subject compounds will be administered in a pharmaceutically acceptable formulation or composition. Examples of such formulations include injectable solutions, tablets, milk, or suspensions, creams, oil-in-water and water-in-oil emulsions, microcapsules and microvesicles.

These compositions will comprise conventional pharmaceutical excipients and carriers typically used in drug formulations, e.g., water, saline solutions, such as phosphate buffered saline, buffers, surfactants.

The subject compounds may be free or entrapped in microcapsules, in colloidal drug delivery systems such as liposomes, microemulsions, and macroemulsions. Suitable materials and methods for preparing pharmaceutical formulations are disclosed in Remington's Pharmaceutical Chemistry, 16' Edition, (1980). Also, solid formulations containing the subject compounds, such as tablets, and capsule formulations, may be prepared.

Suitable examples thereof include semipermeable materials of solid hydrophobic polymers containing the subject compound which may be in the form of shaped articles, e.g., films or microcapsules, as well as various other polymers and copolymers known in the art.

The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight.

The subjects treated will typically comprise mammals and most preferably will be human subjects, e.g., human cancer subjects.

The compounds of the invention may be used alone or in combination. Additionally, the treated compounds may be utilized with other types of treatments, e.g., cancer treatments. For example, the subject compounds may be used with other chemotherapies, e.g., tamoxifen, taxol, methothrexate, biologicals, such as antibodies, growth factors, lymphokines, or radiation, etc. Combination therapies may result in synergistic results.

The preferred indication is cancer, especially the cancers identified previously.

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof. All publications, issued patents and patent applications referred to herein are incorporated by reference thereto, including but not limited to U.S. Ser. No. 09/339,948, now U.S. Pat. No. 6,245,754; U.S. Provisional Application Ser. No. 60/223, 421; U.S. Provisional Application Ser. No. 60/223,724; U.S. Provisional Application Ser. No. 60/235,269; and U.S. Provisional Application Ser. No. 60/235,270.

What is claimed:

1. A 3-deoxy-D-myo-inositol analog having the formula:

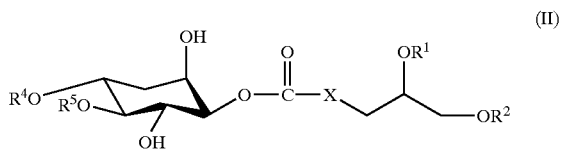

(II)

wherein X is O or $CH_2$; $R^1$ and $R^2$ are individually, $(C_1-C_{25})$ alkyl, $(C_6-C_{10})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl, $(C_9-C_{32})$ alkenylaryl or $C(O)R^3$; and $R^3$ is $(C_1-C_{25})$ alkyl, $(C_6-G_{102})$ aryl, $(C_3-C_8)$ cycloalkyl, $(C_2-C_{22})$ alkenyl, $(C_5-C_8)$ cycloalkenyl, $(C_7-C_{32})$ aralkyl, $(C_7-C_{32})$ alkylaryl, $(C_9-C_{32})$ aralkenyl or $(C_9-C_{32})$ alkenylaryl; $R^4$ and $R^5$ are individually hydrogen or a phosphate group; or when $R^4$ or $R^5$ is not hydrogen, a pharmaceutically acceptable salt thereof.

2. A method of therapy which results in the inhibition of PtdIns-3-kinase in a subject in need of such inhibition which comprises administering a therapeutically effective amount of at least one compound according to claim 1.

3. The method of claim 2, wherein said compound antagonizes myo-inositol cell growth signalling.

4. The method of claim 2, wherein said method results in the inhibition of cell proliferation and/or differentiation.

5. The method of claim 2, wherein said compound is 1-O-octadecyl-2-O-methyl-sn-glycero-3-phospho-1D-3-deoxy-myo-inositol, 1-O-octadecyl-2-O-methyl-sn-glycero-3-phosphono-1D-3-deoxy-myo-inositol, or 1-O-octadecyl-2-O-methyl-sn-glycero3-phosphono-1D-3-deoxy-myo-inositol.

6. The method of claim 2, which results in the induction of cell apoptosis.

7. The method of claim 2, wherein said compound is administered by a method selected from the group consisting of oral, intranasal, intraperitoneal, intravenous, intramuscular, intratumoral, rectal and transdermal.

8. The method of claim 2, wherein the administered amount of said compound ranges from 1 mg to 1 g/kg of the said weight of said subject.

9. The method claim 8, wherein the amount of said compound ranges from 5 mg to 50 mg/kg of the weight of said subject.

* * * * *

UNITED STATES PATENT AND TRADEMARK OFFICE
CERTIFICATE OF CORRECTION

PATENT NO.       : 6,667,340 B1                                      Page 1 of 1
APPLICATION NO.  : 09/879765
DATED            : December 23, 2003
INVENTOR(S)      : Kozikowski et al.

It is certified that error appears in the above-identified patent and that said Letters Patent is hereby corrected as shown below:

Please add at column 1, line 19:

Federal Research Sponsorship:

This invention was made with support from the U.S. government under grants from the U.S. National Institutes of Health, contract numbers CA061015-09 and CA052995-18. The U.S. government has certain rights in this invention.

Signed and Sealed this

Second Day of December, 2008

JON W. DUDAS
*Director of the United States Patent and Trademark Office*